United States Patent
Engmark et al.

(10) Patent No.: US 8,473,056 B2
(45) Date of Patent: Jun. 25, 2013

(54) ASSEMBLY METHOD FOR IMPLANTABLE MEDICAL DEVICE

(75) Inventors: David B. Engmark, Bethel, MN (US); Gary M. Grose, Brooklyn Park, MN (US); Todd H. Schaefer, Blaine, MN (US); Thomas I. Ceballos, Spring Lake Park, MN (US); Andrew J. Ries, Lino Lakes, MN (US)

(73) Assignee: Medtronic, Inc., Minnesota, MN (US)

( * ) Notice: Subject to any disclaimer, the term of this patent is extended or adjusted under 35 U.S.C. 154(b) by 1461 days.

(21) Appl. No.: 12/109,838

(22) Filed: Apr. 25, 2008

(65) Prior Publication Data
US 2009/0266573 A1 Oct. 29, 2009

(51) Int. Cl.
*A61N 1/08* (2006.01)

(52) U.S. Cl.
USPC ..................... 607/36; 607/5; 607/9

(58) Field of Classification Search
USPC ............ 607/36, 5, 9, 2, 4; 128/899; 381/322; 257/685; 361/517–519, 535–537; 174/50, 174/50.5, 50.52
See application file for complete search history.

(56) References Cited

U.S. PATENT DOCUMENTS

| 4,481,950 | A | 11/1984 | Duggan |
| 5,103,818 | A | 4/1992 | Maston et al. |
| 5,674,260 | A | 10/1997 | Weinberg |
| 6,026,325 | A * | 2/2000 | Weinberg et al. ............... 607/36 |
| 6,247,474 | B1 * | 6/2001 | Greeninger et al. .......... 128/899 |
| 6,259,188 | B1 | 7/2001 | Woodard |
| 6,409,675 | B1 | 6/2002 | Turcott |
| 7,020,525 | B1 | 3/2006 | Davis et al. |
| 7,211,884 | B1 | 5/2007 | Davis |
| 2003/0040779 | A1 | 2/2003 | Engmark et al. |
| 2003/0088293 | A1* | 5/2003 | Clarke et al. .................... 607/36 |
| 2006/0009818 | A1 | 1/2006 | Von Arx |
| 2006/0149329 | A1 | 7/2006 | Penner |

OTHER PUBLICATIONS (PCT/US2009/041346) PCT Notification of Transmittal of the International Search Report and the Written Opinion of the International Searching Authority, 5 pages, Published Oct. 29, 2009.

* cited by examiner

*Primary Examiner* — Kennedy Schaetzle
*Assistant Examiner* — Erica Lee

(57) ABSTRACT

An implantable medical device (IMD) having a hermetic housing formed from a case and a cover each having an exterior surface and an interior surface. An IMD component is mounted to the interior surface of the cover and has an electrical contact. A hybrid circuit is assembled in the case. The IMD component electrical contact is electrically coupled to the to the hybrid circuit assembled in the case.

9 Claims, 15 Drawing Sheets

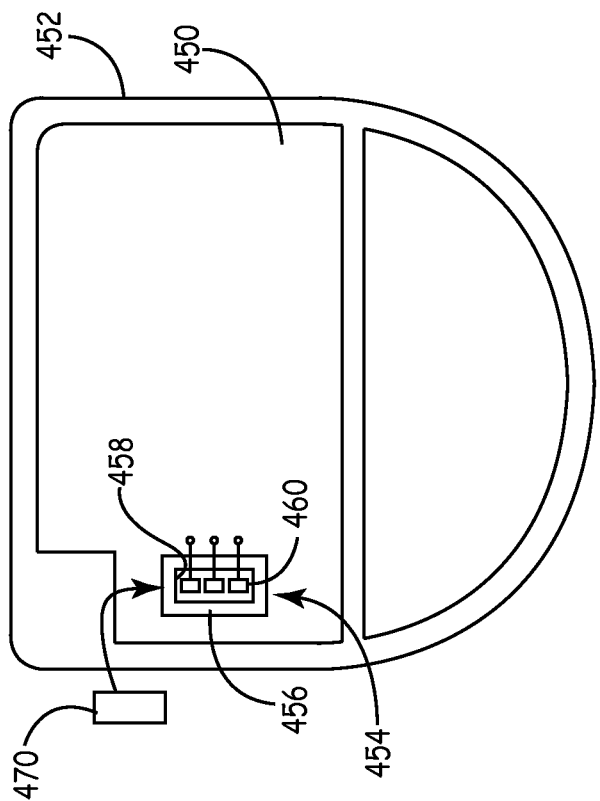
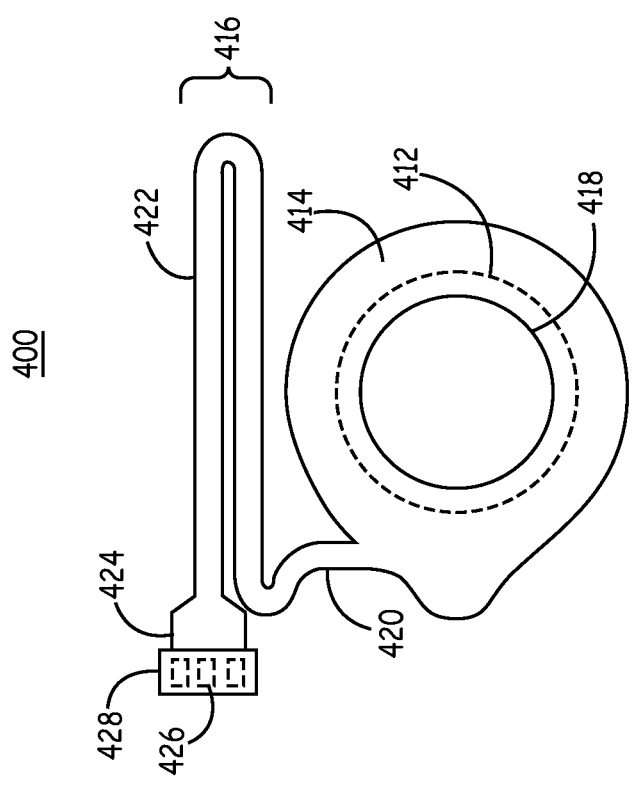
FIG. 15B
FIG. 15A

ASSEMBLY METHOD FOR IMPLANTABLE MEDICAL DEVICE

TECHNICAL FIELD

The disclosure relates generally to implantable medical devices and, in particular, to a method for assembling an implantable medical device having components mounted to an interior surface of the device housing.

BACKGROUND

Implantable medical devices (IMDs), such as pacemakers, cardioverter defibrillators, drug pumps, neurostimulators, and the like, include electronic circuitry enclosed within a hermetically sealed housing. The housing is typically formed of two shield halves, referred to herein as a case and a cover, that are welded together. One method for assembling an IMD such as an implantable cardioverter defibrillator (ICD) involves setting a battery and capacitor in the case, placing a hybrid circuit over the battery, and placing any additional components, such as communication circuitry, over the capacitor. All necessary electrical connections can then be made between the hybrid circuit and other ICD components stacked together in the case. After electrical connections are made and any testing is performed, the cover is placed over the case and the housing welded closed. This method of assembly can be generally referred to as a "top-down" assembly method since all IMD components are stacked together in the case and the cover is then placed over the case. Other assembly methods involve assembling and electrically coupling all of the circuitry and components together then placing the assembled component into the housing as one unit and closing the housing.

In some circumstances, however, it is desirable to include components mounted to an interior surface of the IMD housing. For example, a piezoelectric transducer used to generate an audible patient alert may be mounted to an interior surface of the housing to cause the housing to resonate, thereby improving the patient alert function of the IMD. Methods are needed for assembling an IMD having electrical components mounted to an interior surface of the housing which still allows a top-down assembly of the device.

BRIEF DESCRIPTION OF THE DRAWINGS

FIG. 15A is a plan view of a flexible circuit having an alternative electrical connector.

FIG. 15B is a top plan view of a hybrid circuit assembled in an IMD case for use with the flexible circuit of FIG. 15A.

DETAILED DESCRIPTION

Figure 1:
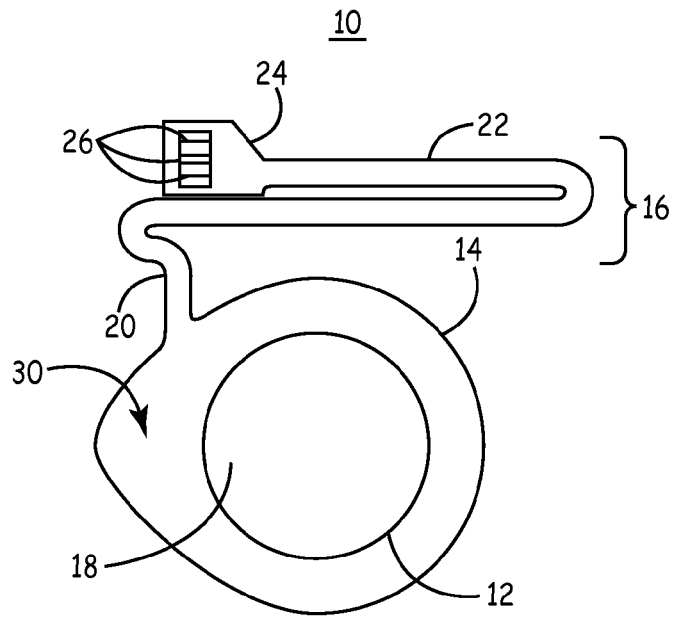
FIG. 1 is a top plan view of a flexible circuit for mounting along an interior surface of an IMD housing.
Figure 2A:
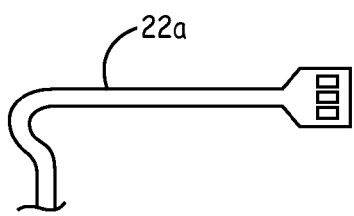
FIG. 2A through FIG. 2D illustrate alternative extender geometries for the connector shown in FIG. 1.
Figure 2B:
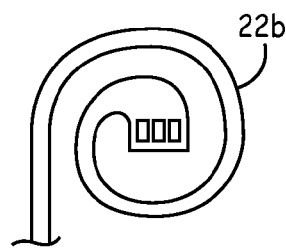
Figure 2C:
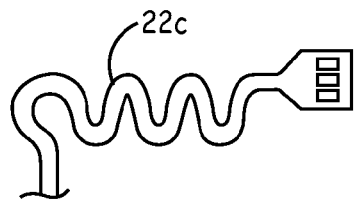
Figure 2D:
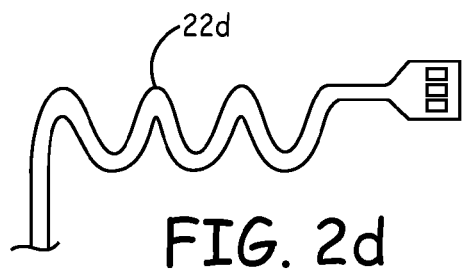

In the following description, references are made to illustrative embodiments. It is understood that other embodiments may be utilized without departing from the scope of the invention. For purposes of clarity, the same reference numbers are used in the drawings to identify similar elements. Unless otherwise noted, drawing elements are not shown to scale.

FIG. 1 is a top plan view of a flexible circuit for mounting along an interior surface of an IMD housing. As used herein a "flexible circuit" refers generally to a combination of conductors and/or electrical components mounted on a bendable film, which acts as an insulating (dielectric) base material, and covered with an insulating cover layer. Flexible circuit 10 includes a flexible circuit substrate 14 incorporating an IMD electrical component 12, a connector 16, and a coupling area 18. An "IMD electrical component" or just "IMD component" refers to an active component that receives and/or generates an electrical signal that is carried by electrical conductors and connectors to/from other IMD electrical components. The IMD electrical component actively performs an IMD operation in contrast to passive electrical conductors or connectors that route electrical signals between IMD components. IMD components may include sensors, antennas, therapy delivery components, and the like.

In one embodiment, electrical component 12 is embodied as a piezoelectric transducer used for generating an audible patient alert signal by causing the IMD housing (not shown in FIG. 1) to resonate upon activation of transducer 12. Piezoelectric transducer 12 may be a commercially available transducer, for example as provided by Kyocera Corporation, Japan. It is recognized that piezoelectric transducer 12 may alternatively be implemented as a sensing element for detecting physiological sounds such as heart sounds, lung sounds, and intestinal sounds. It is further contemplated that other IMD electrical components may be included or substituted in flexible circuit 10 according to the needs of a particular application. For example other sensors or communication elements that perform more efficiently or effectively, or provide greater volume efficiency within the IMD, by being mounted along an interior surface of the IMD housing may be included in flexible circuit 10. As such, embodiments of the present invention are not limited to a flexible circuit incorporating a piezoelectric transducer. Embodiments may include any IMD electrical component mounted to an interior surface of the IMD cover that requires electrical connection across the cover and case to other IMD circuitry assembled in the case.

Coupling area 18 is provided for mounting flexible circuit 10 to an interior surface of the IMD housing. The top surface 30 of flexible circuit 10 shown in the top view of FIG. 1 is the surface that will be against the IMD housing interior surface after IMD assembly is complete. Coupling area 18 is coated with an adhesive, a tape, or other coupling medium to allow physical mounting of transducer 12 (within flexible circuit 10) to the IMD housing interior surface. In one embodiment, as will be further described herein, coupling area 18 is covered by a pressure sensitive adhesive having a removable backing that remains in place until transducer 12 is mounted to the housing surface.

Flexible connector circuit 16 is provided to enable electrical connection of flexible circuit 10 to a hybrid circuit (not shown) included in the IMD. A "flexible connector circuit" as used herein refers to a combination of electrical conductors formed on a bendable insulating base layer and covered with a bendable insulating cover layer. The flexible connector circuit 16 routes electrical signals between IMD components. A flexible connector circuit may include contacts and/or connectors for electrically coupling the flexible connector circuit to other IMD components or circuits. In some embodiments of the invention, the flexible connector circuit does not include any active IMD components but includes only conductors, contacts and optionally electrical connectors for routing electrical signals to/from IMD components. Achieving electrical connection between components mounted to an interior surface of one shield half of an IMD housing to components assembled in the other shield half of the IMD housing can be a challenge while still maintaining ease of assembly. For example, if piezoelectric transducer 12 is mounted directly to an interior surface of an IMD housing cover, electrical connection of transducer 12 to a hybrid circuit assembled in the IMD case can be a tedious and cumbersome task. Embodiments of the present invention address this challenge by providing methods for mounting components to a housing interior surface and electrically coupling those components to the IMD hybrid circuit.

Connector circuit 16 shown in FIG. 1 is formed as a continuous extension of flexible circuit 10. In other embodiments described below, a flexible connector circuit can be formed as a separate flexible circuit that is electrically coupled to the flexible circuit 10 using electrical connectors and/or coupling methods. Flexible connector circuit 16 includes a laterally extending arm portion 20 which forms an attached proximal end, an electrical contact portion 24 which forms a free distal end, and an elongated extender portion 22 extending between the attached arm 20 and the free electrical contact portion 24. Electrical contact portion 24 includes exposed electrical contacts 26. Contacts 26 are coupled to conductive traces (not shown) extending through flexible connector circuit 16 to contacts or attachment points (not shown) on transducer 12. The flexible connector circuit 16 having elongated extender portion 22 allows flexible and reliable electrical connection between transducer 12 and the IMD hybrid circuit, as will be further described herein, when the flexible circuit 10 is mounted inside a housing cover and the hybrid circuit is assembled in the case.

Elongated extender portion 22 is shown having an elongated serpentine configuration in FIG. 1. Extender portion 22 includes two U-shaped curves and two parallel segments, however it is recognized that if additional length of connector 16 is desired, extender 22 may be manufactured with additional curves and parallel segments. Furthermore, it is recognized that extender portion 22 may be formed in a variety of geometries which would provide flexible extension of electrical contacts 26 away from transducer 12 to facilitate electrical connection of contacts 26 to an IMD hybrid circuit. Some alternative extender geometries are shown in FIG. 2. Connector 16 may include a linear extender portion 22a, a curved or coiled extender portion 22b, a short-axis serpentine extender portion 22c (as compared to the long-axis serpentine extender 22 of FIG. 1), or a zig-zag extender portion 22d. Each of these configurations of extender 22 allow contacts 26 to be extended a distance away from transducer 12, giving more working space to perform electrical coupling methods, but allow connector 16 to regain a normally flattened, volumetrically efficient, geometry upon closure of the IMD housing, without bending or creasing of the conductive electrical traces formed within the flexible connector circuit 16.

Using standard round or flat wires to electrically couple the transducer 12 across an IMD housing cover to circuitry within an IMD housing case can result in strain imposed on the wires and wire connections when the housing is closed since the wires will have to bend, crease, and/or curve to conform to a compact configuration within the limited volume of the IMD housing. The wires will not always route consistently when the IMD is closed resulting in unintended strain or compression on IMD components. The normally flat geometry of the flexible connector circuit 16 minimizes strain on the conductive traces and the electrical connections upon closure of the IMD housing, has minimal thickness which does not significantly add to tolerance specifications of the IMD housing and other components in all three dimensions. The shape retention of the flexible connector circuit results in consistent routing of the connector circuit and eliminates the need to bend or crease connector circuit 16 upon closure of the case and cover. The term "consistent routing" as used herein with regard to a connector refers to a predictable and consistent geometry of the connector whenever the case and cover are closed as opposed to a random or unpredictable geometry which can occur, for example, with the use of standard wire connectors.

Figure 3:
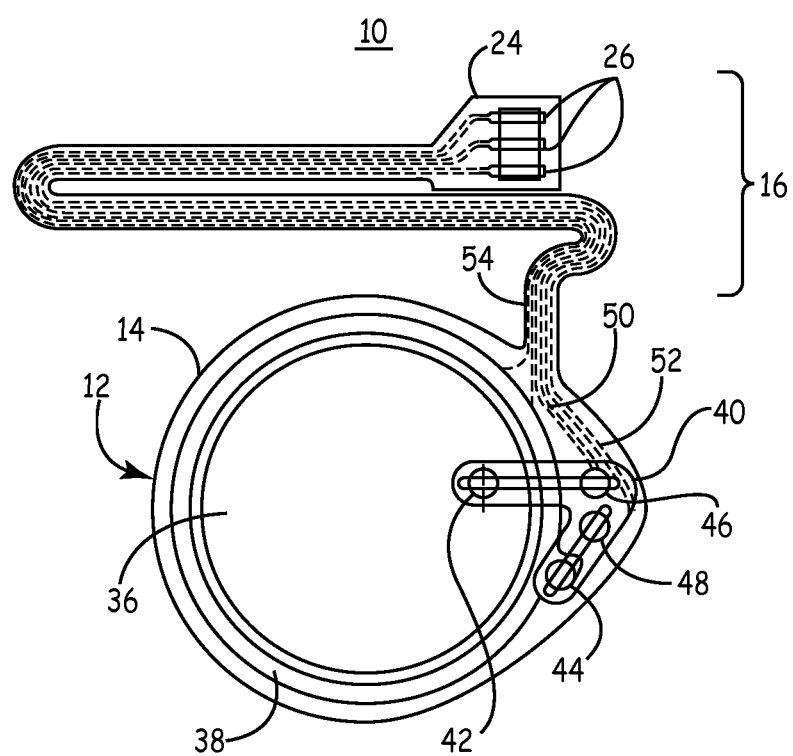
FIG. 3 is a bottom view of the flexible circuit of FIG. 1.

FIG. 3 is a bottom view of flexible circuit 10. A jumper connector 40 allows electrical connection between piezoelectric transducer 12 and conductive traces 50 and 52 formed in the flexible substrate 14. Jumper connector 40 includes a ceramic attachment 42 for electrically coupling to the ceramic portion 36 of transducer 12 and a brass attachment 44 for electrically coupling to the brass portion 38 of transducer 12. While not explicitly shown in FIG. 3, it is understood that ceramic portion 36 includes a metallized or plated area to enable electrical connection thereto. A ceramic attachment trace 50 formed in the flexible substrate 14 is electrically coupled to a ceramic connector 46 on jumper 40. A brass attachment trace 52 formed in flexible substrate 14 is electrically coupled to brass connector 48 on jumper 40. A cover layer is not shown in FIG. 3 but, as will be described below, will cover the transducer 12 and jumper 40 in the final assembly of flexible circuit 10.

The ceramic trace 50, the brass trace 52, and a ground trace 54 extending from a copper layer (not shown) in flexible substrate 14 each extend through connector circuit 16 to respective electrical contacts 26 on electrical contact pad portion 24.

Figure 4:
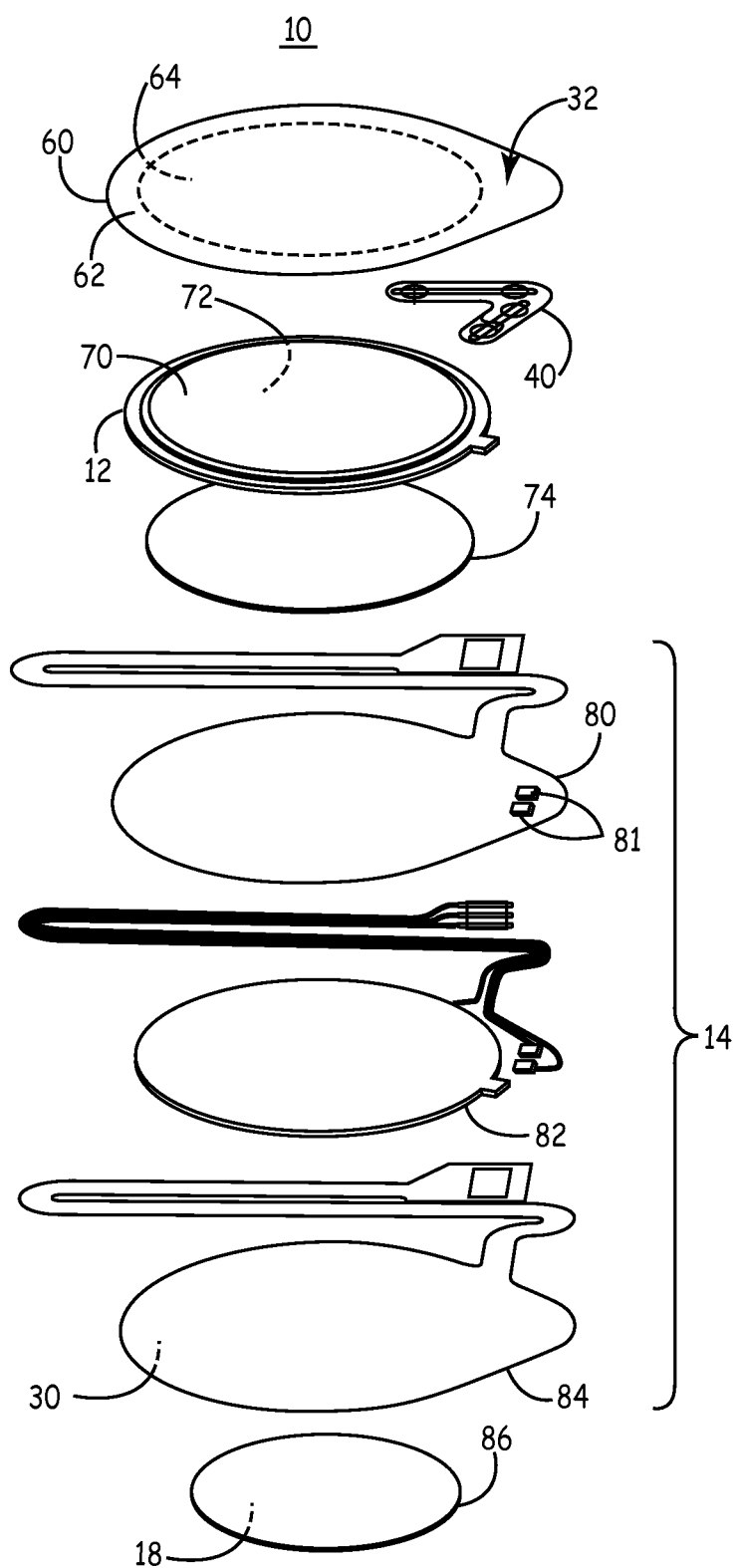
FIG. 4 is an exploded view of the flexible circuit of FIG. 1.

FIG. 4 is an exploded view of flexible circuit 10. A cover layer 60 forms the bottom surface 32 of the flexible circuit 10, which will face toward the interior space of the IMD housing after final assembly. Cover layer 60 may be formed of polyimide with an adhesive ring 62 formed along the inner surface 64 of cover layer 60. Inner surface 64 is placed against a bottom surface 70 of the transducer 12. Jumper 40 is attached to transducer 12 and is positioned between transducer 12 and cover layer 60.

A pressure sensitive adhesive layer 74 couples transducer bottom surface 72 to a bottom insulating layer 80 of flexible substrate 14. Flexible substrate 14 includes bottom insulating layer 80, copper layer 82, and top insulating layer 84. Bottom layer 80 may be formed from polyimide with full coverage of an adhesive for securely attaching bottom layer 80 to copper layer 82. Bottom layer 80 includes openings 81 through which electrical connections between jumper 40 and copper layer 82 can be made.

A top insulating layer 84 of flexible substrate 14 may be formed of polyimide with full coverage of an adhesive to securely attach to the opposite side of copper layer 82 such that copper layer 82 is "sandwiched" between top and bottom insulating layers 84 and 80 to form flexible substrate 14. Copper layer 82 forms a ground plane for shielding the brass layer of the transducer 12 from the IMD housing when the IMD housing serves as an active electrode, for example as an active electrode in delivering defibrillation shocks when the IMD is embodied as an ICD.

Finally, a pressure sensitive adhesive layer 86 is coupled to the top surface 30 of top insulating layer 84 to form the top surface coupling area 18 of flexible circuit 10.

Figure 5:
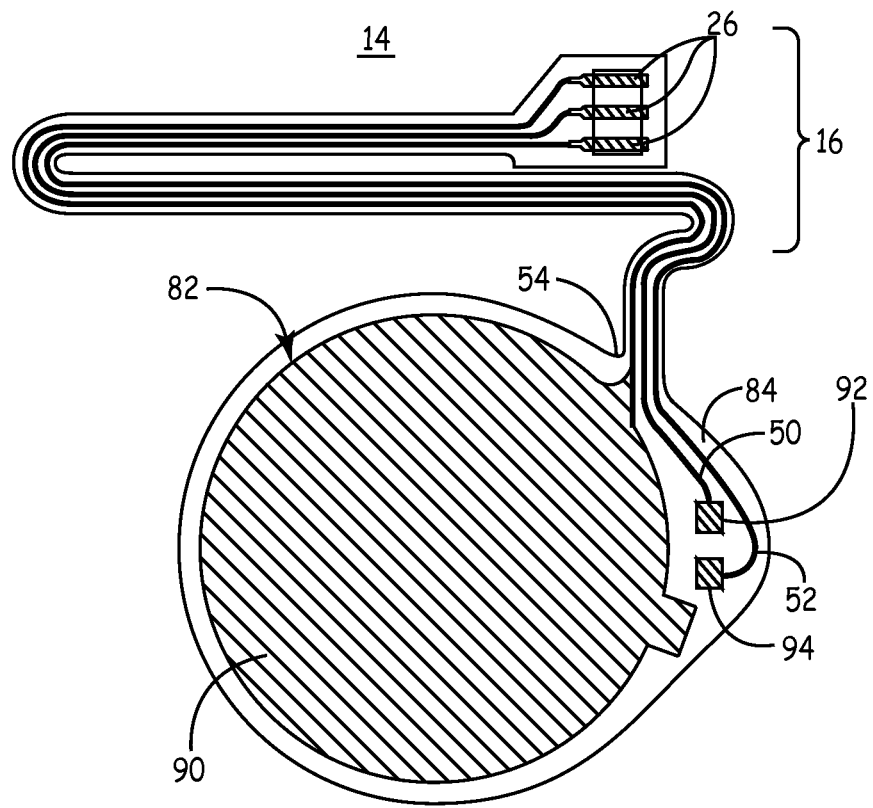
FIG. 5 is a bottom plan view of the flexible substrate of the circuit of FIG. 1 with the bottom insulating layer removed.

FIG. 5 is a bottom plan view of flexible substrate 14 with the bottom insulating layer removed. As such, top insulating layer 84 and copper layer 82 of flexible substrate 14 are shown in FIG. 5. Copper layer 82 formed on top insulating layer 84 includes a ground plane 90 from which ground trace 54 extends along flexible connector circuit 16 to one of the contacts 26. Copper layer 82 further includes contact pads 92 and 94 for electrically coupling to jumper 40 through openings 81 of bottom insulating layer 80 (jumper 40, openings 81 and bottom insulating layer 80 all shown in FIG. 4). The ceramic attachment trace 50 extends from a ceramic contact pad 92, along connector 16 to a respective one of contacts 26. Likewise, brass attachment trace 52 extends from a brass contact pad 94, along connector 16, to a respective one of contacts 26.

Figure 6:
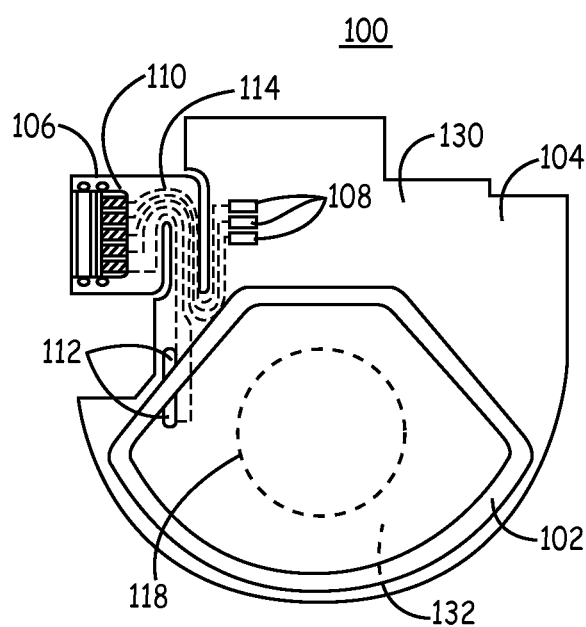
FIG. 6 is a top plan view of a second flexible circuit included in an IMD for interfacing with the flexible circuit of FIGS. 1 through 5.

FIG. 6 is a top plan view of a second flexible circuit included in an IMD for interfacing with the piezoelectric transducer flexible circuit of FIGS. 1 through 5. In one embodiment of the invention, the flexible circuit 10 incorporating piezoelectric transducer 12 is configured to interface with an antenna flexible circuit 100 during IMD assembly. Antenna flexible circuit 100 includes an antenna 102, incorporated in a flexible substrate 104, and a connector 106. Antenna flexible circuit 100 further includes contact pads 108 for coupling to each of the contacts 26 of flexible circuit 10 (FIG. 1). Connector 106 includes individual contacts 110 each coupled to respective traces 114 (shown by dashed line) extending through antenna flexible substrate 104 to a respective one of the contact pads 108 for coupling to flexible circuit 10 or to one of antenna contacts 112. Connector 106 is used to electrically couple antenna flexible circuit 100 to an IMD hybrid circuit (not shown) as will be further described herein. Electrical connection of piezoelectric transducer flexible circuit 10 to the IMD hybrid circuit is thus made via antenna flexible circuit 100.

The top side 130 of circuit 100 shown in FIG. 6 will face the transducer flexible circuit 10 when the IMD is fully assembled. The bottom side 132 will face toward the IMD interior space and includes a coupling area 118 for mounting antenna flexible circuit 100 onto another IMD component, assembled in the case such as an IMD capacitor. Coupling area 118 may be covered, for example, with a pressure sensitive adhesive layer.

Figure 7:
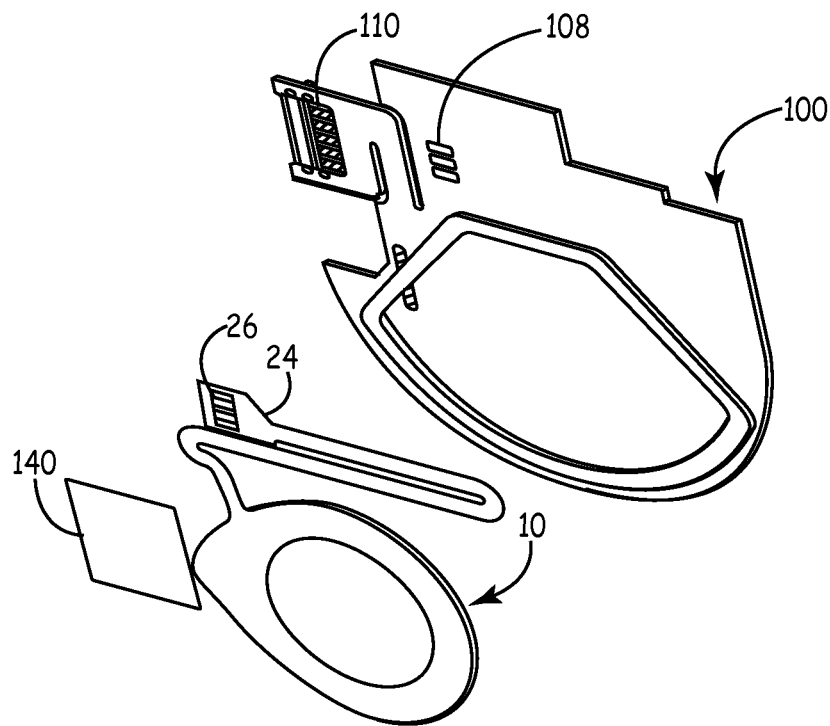
FIG. 7 is a perspective view of the flexible circuit of FIG. 1 being assembled with the second flexible circuit of FIG. 6.

FIG. 7 is a perspective view of the flexible circuit 10 being assembled with the antenna flexible circuit 100. Contacts 26 on flexible circuit 10 are electrically coupled to contact pads 108 of flexible circuit 100, for example by brazing or soldering such that the piezoelectric transducer included in circuit 10 is electrically coupled to contact pads 108. Contact pads 108 are coupled to antenna flexible circuit contacts 110 via traces extending within flexible circuit 100 as described above. After coupling contacts 26 to contact pads 108, an insulating layer 140, for example an adhesive polyimide tape, is applied over the electrical contact portion 24 of circuit 10 to insulate and protect the electrical connections and promote secure attachment of electrical contact portion 24 to the contact pads 108 of flexible circuit 100.

Figure 8:
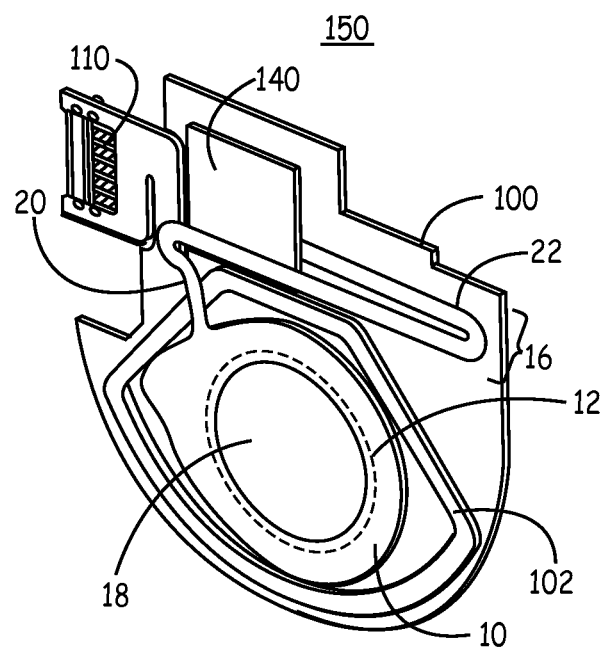
FIG. 8 is a perspective view of the completed flexible circuit assembly.

The completed flexible circuit assembly 150 is shown in FIG. 8. Flexible circuit 10 is positioned over antenna flexible circuit 100 such that piezoelectric transducer 12 is nested within the antenna 102 incorporated in flexible circuit 100. The laterally extending arm 20 of flexible connector 16 crosses over antenna 102 such that extender 22 positions electrical contact portion 24 (not shown in FIG. 8) over contact pads 108 (not shown) of flexible antenna circuit 100. Insulating layer 140 secures the electrical connection between flexible circuit 10 and antenna flexible circuit 100. The entire flexible circuit assembly 150 may then be stacked with other IMD components in an IMD case and electrical connections made between contacts 110 and the IMD hybrid circuit. Flexible circuit 10 may then be lifted off antenna flexible circuit 100 to mount circuit 10 to the inside of a housing cover along coupling area 18. Extender 22 can be described as having a normally planar position which can expand in a direction perpendicular to its normally planar position to allow flexible circuit 10 to be pulled away from flexible circuit 100 while maintaining electrical connection thereto. Closure of the case and cover will return extender 22 to its normally flat, generally planar geometry. The shape retention of flexible connector circuit 16 results in consistent routing of the flexible connector circuit 16 upon closure of the case and cover.

In an alternative assembly method, circuit 10 may first be mounted along the inside of the IMD housing cover and antenna circuit 100 assembled in the IMD case over a hybrid circuit. The electrical connections between connector 16 and flexible circuit 100 may be made by extending extender portion 22 toward flexible circuit 100 to position contacts 26 against contact pads 108. Next the case and cover are closed, returning extender to its normally flat geometry.

Figure 9:
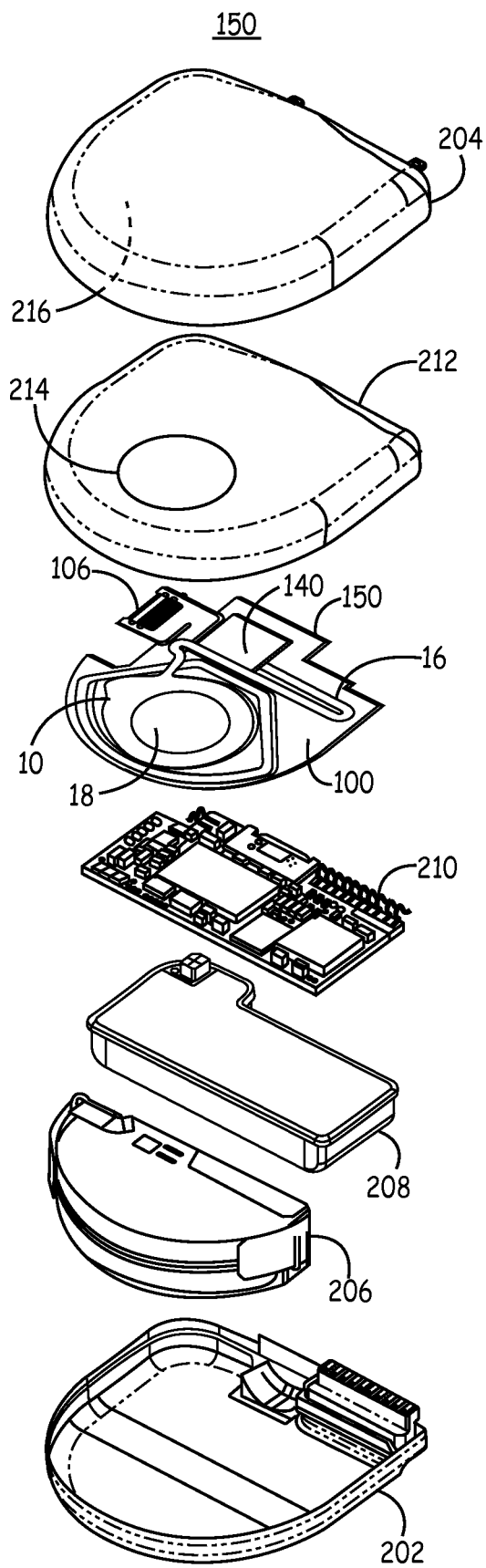
FIG. 9 is an exploded perspective view of an IMD assembled with the flexible circuit assembly of FIGS. 7 and 8.

FIG. 9 is an exploded perspective view of an IMD 200 assembled with the flexible circuit assembly 150 of FIGS. 7 and 8. In an assembly method, a capacitor 206 and battery 208 are placed in a case 202. Hybrid circuit 210 is placed over the battery 208 and electrical connections between the circuit 210, battery 208 and capacitor 206 are made. The flexible circuit assembly 150, including the flexible antenna circuit 100 and the flexible circuit 10 as shown in FIG. 7, is placed over the capacitor 206 and hybrid circuit 210. The pressure sensitive adhesive layer 118 (shown in FIG. 6) is used to couple antenna flexible circuit 100 to capacitor 206. Electrical connections are then made between connector 106 of antenna flexible circuit 100 and hybrid circuit 210.

An insulator 212 is placed within cover 204. Insulator 212 is provided with an opening 214 corresponding to coupling area 18 of flexible circuit 10. Insulator 212 may not be necessary in all applications but is shown here in the case of an "active can" ICD. Flexible circuit 10 is then lifted off antenna flexible circuit 100 and coupling area 18 is secured to the interior surface 216 of cover 204, through opening 214. Flexible elongated connector 16 allows flexible circuit 10 to be extended away from antenna flexible circuit 100 and case 202 while maintaining electrical connection between flexible circuit 10 and antenna flexible circuit 100 (beneath insulating layer 140). Extension of flexible circuit 10 away from case 202 provides space for handling circuit 10 during mounting of circuit 10 into cover 204. Cover 204 is then assembled with case 202 and hermetically sealed. As such, flexible circuit assembly 150 allows a "top down" assembly method of IMD components into case 202 with cover 204 placed down last over case 202. Elongated flexible connector 16 provides electrical connection across the case 202 and cover 204 before and after closure of the case and cover.

Figure 10:
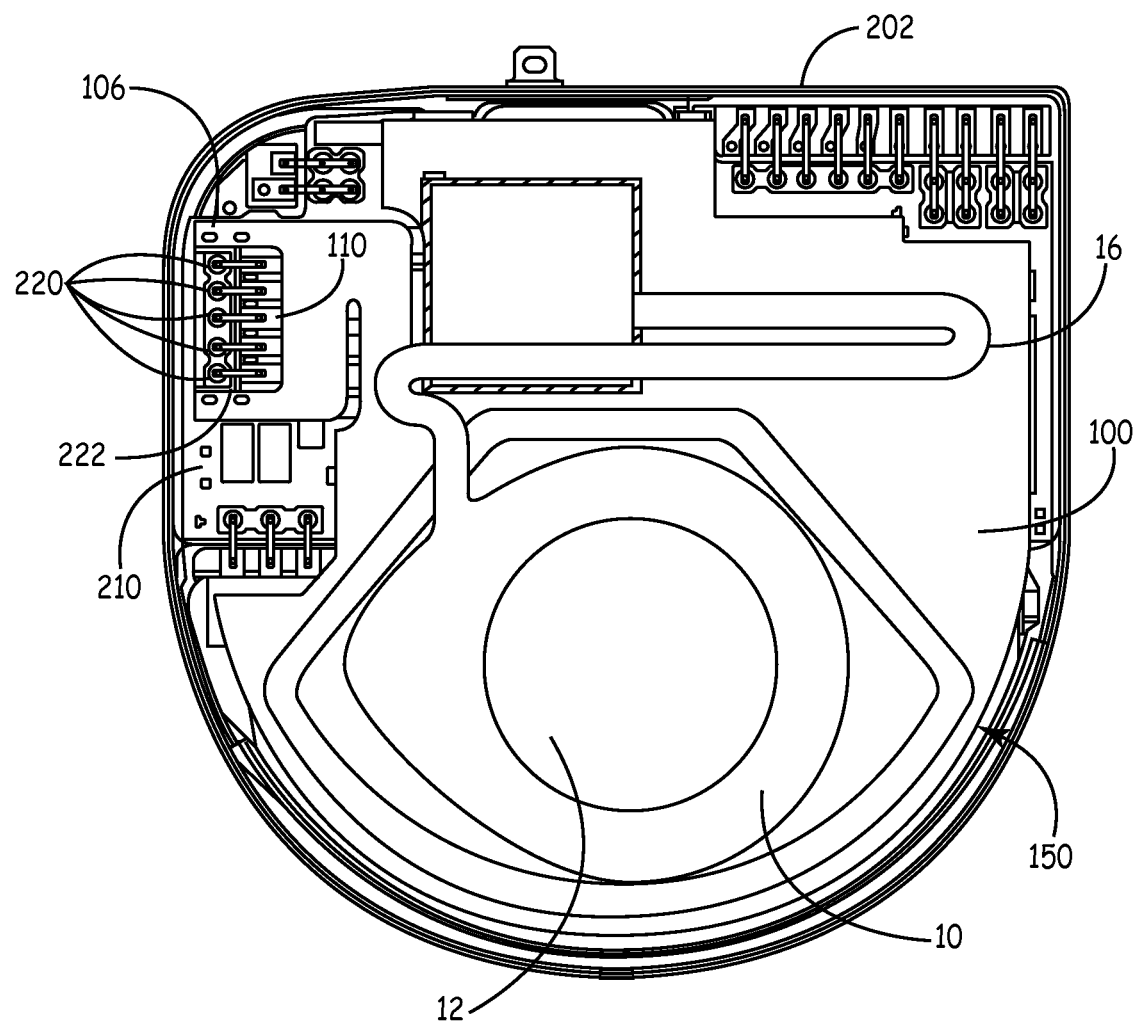
FIG. 10 is a top plan view of the IMD of FIG. 9.

FIG. 10 is a top plan view of the flexible circuit assembly 150 and other IMD components assembled in case 202. Connector 106 is placed over contact pads 220 of hybrid circuit 210. Electrical connection between contacts 110 of antenna flexible circuit 100 and contact pads 220 can be accomplished in a variety of ways. In one embodiment, laser ribbon bonds 222 are formed between contact pads 220 and contacts 110 to electrically couple antenna flexible circuit 100, and thereby flexible circuit 10, to hybrid circuit 210. Flexible circuit assembly 150 may be referred to as a "split flexible circuit" because the circuitry coupling the transducer 12 to the hybrid circuit 210 extends through two separate flexible circuits 10 and 100 which are electrically coupled together via a flexible circuit connector 16.

Figure 11:
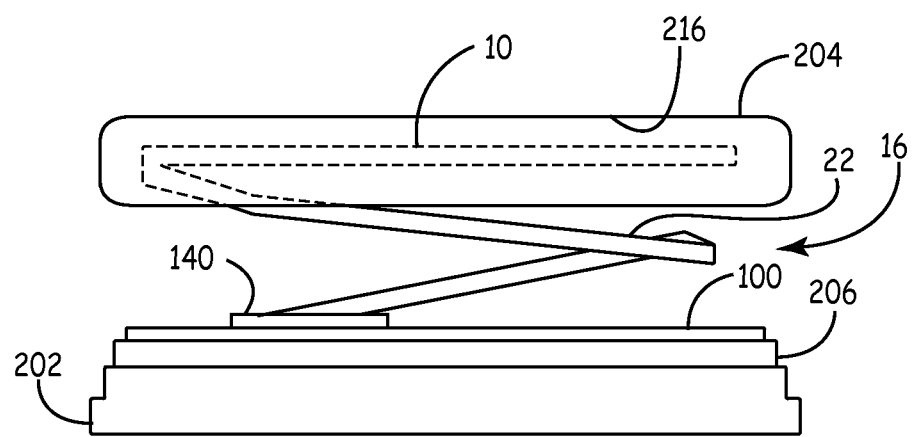
FIG. 11 is a side plan view of the IMD of FIG. 9 showing the flexible connector circuit extending from the flexible circuit mounted in the IMD cover.

FIG. 11 is a side plan view showing extension of the flexible circuit connector 16. Flexible circuit 10 is mounted to the interior surface 216 of cover 204. Antenna flexible circuit 100 is assembled in case 202, overlying capacitor 206. Extender 22 of flexible connector circuit 16 is shown in an extended position, expanded generally perpendicularly from its normally flattened, planar geometry in order to extend the contact portion 24 (not shown) away from flexible circuit 10 toward flexible circuit 100, where it is joined to circuit 100 beneath insulator layer 140. The split flexible circuit design allows electrical connections to cross between the case 202 and cover 204 during a "top down" assembly method. Extension of extender 22 by expansion from its normally flattened geometry provides more space for an operator to perform electrical connections after flexible circuit 10 is mounted in cover 204, or in an alternative method, mount circuit 10 in cover 204 after electrical connections between flexible circuit 10 and 100 have already been made. Extender 22 resumes its normally flattened geometry as shown in FIG. 9 upon closure of cover 204 and case 202 for volumetric efficiency.

Figure 12:
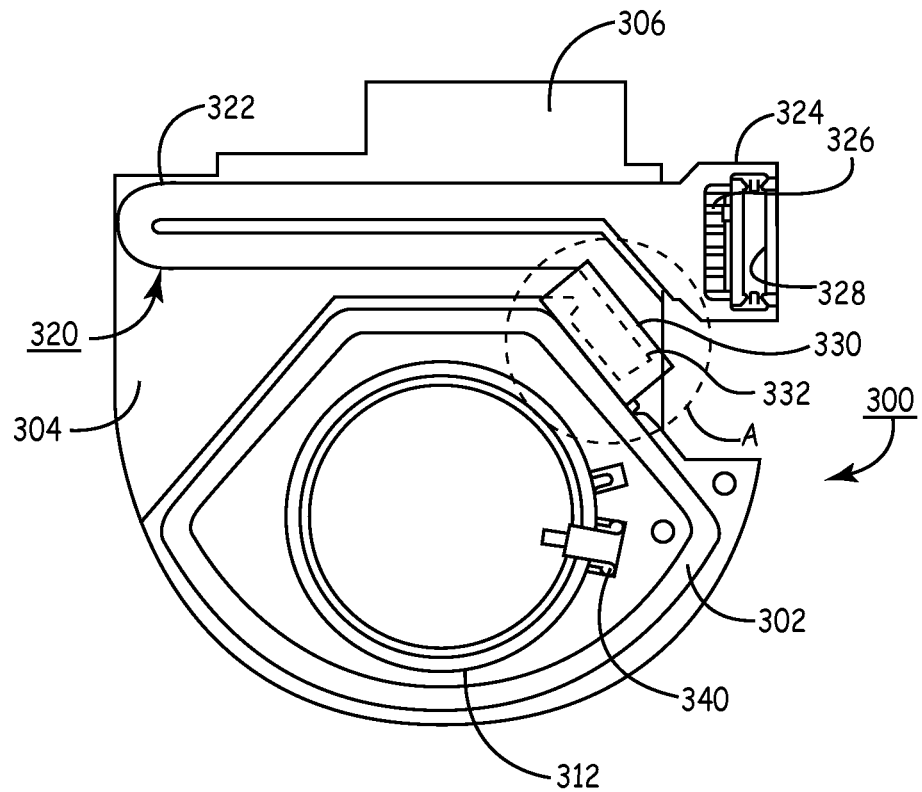
FIG. 12 is a bottom plan view of a flexible circuit according to an alternative embodiment of the invention.

FIG. 12 is bottom plan view of a flexible circuit connector according to an alternative embodiment of the invention. In FIG. 12, flexible circuit connector 320 is formed as a unitary flexible circuit that is used to electrically couple an IMD component mounted in an IMD cover to circuitry assembled in an IMD case. The bottom view of FIG. 12 shows the bottom surface 306 of flexible circuit 300 which will face inward, toward the interior space of the IMD housing, after complete assembly. In this embodiment, flexible circuit 300 includes both an antenna 302 and a piezoelectric transducer 312 in a single flexible circuit. Piezoelectric transducer 312 is mounted on the bottom surface 306 of flexible substrate 304, nesting within antenna 302. A jumper 340 couples the transducer 312 to appropriate traces (not shown) formed in a copper layer (not shown) within flexible substrate 304 as generally described above.

Flexible circuit 300 is electrically coupled to a flexible connector circuit 320. Flexible connector circuit 320 includes a flexible extender 322 extending between a first, proximal, connector portion 332 and a second, distal, connector portion 324. The flexible extender 322 is shown having an elongated serpentine configuration but may have other geometries as described in conjunction with FIG. 2. The proximal connector portion 332 is electrically coupled to flexible circuit 300 as shown in the detail of area A in FIG. 13. The distal connector portion 334 can be extended away from flexible circuit 300 by extension of extender 322 for electrical coupling to an IMD hybrid circuit.

Figure 13:
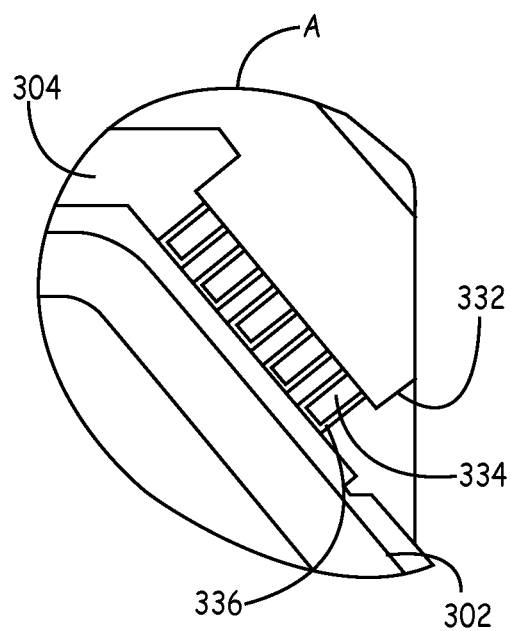
FIG. 13 is a detailed plan view of the proximal connector portion of the flexible connector circuit of FIG. 12.

Proximal connector 332 includes contacts 334 (shown in FIG. 13) electrically coupled to traces (not shown) extending through extender 322 to the distal connector portion 324. As shown in FIG. 13, individual contacts 334 of proximal connector portion 332 are electrically coupled to bonding pads 336 formed in flexible substrate 304. Electrical connection between contacts 334 and bonding pads 336 may be formed by soldering, welding, brazing, applying an electrically conductive adhesive or other suitable methods. An adhesive insulating layer 330 is placed over connector 332, as shown in FIG. 12, to protect the electrical connections between proximal connector 332 and flexible substrate 304. Connection between proximal connector 332 of flexible connector circuit 320 and flexible substrate 304 provides electrical connection from individual contacts 326 of distal connector portion 324 of flexible connector circuit 320 to each of a ground plane (not shown), antenna 302 and transducer 312 within flexible circuit 300.

Extender 322 allows flexible circuit 300 to be coupled to an interior surface of an IMD housing cover and be electrically coupled to a hybrid circuit assembled within an IMD housing case. Opening 328 of distal connector 324 fits over contact pads on the hybrid circuit board to allow electrical connection between the contacts 326 and hybrid circuit board, for example using laser ribbon bonds.

Figure 14:
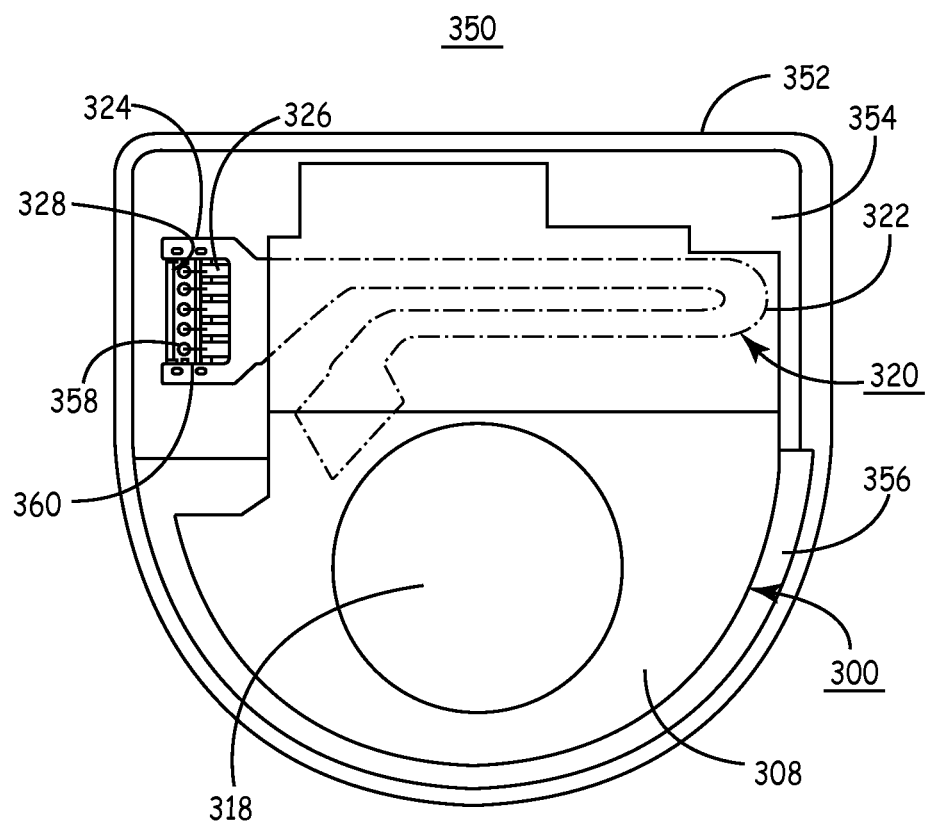
FIG. 14 is a top plan view of an IMD partially assembled with the flexible circuit and flexible connector circuit of FIG. 12.

FIG. 14 is a top plan view of an IMD 350 partially assembled with the flexible circuit 300 and flexible connector circuit 320 of FIG. 12. Flexible circuit 300 is placed over a capacitor 356 and hybrid circuit 354 assembled within case 352 of IMD 350. Flexible connector circuit 320 (shown by dashed dot line) extends between flexible circuit 300 and hybrid circuit 354 and enables electrical connection therebetween. The top surface 308 of flexible circuit 300 will be positioned against the interior surface of the IMD cover (not shown). Distal connector portion 324 is positioned over hybrid circuit 354 such that hybrid circuit contact pads 358 are exposed through opening 328. Laser ribbon bonds 360 are formed between contact pads 358 and contacts 326 of connector portion 324.

Extender 322 allows flexible circuit 300 to be lifted off hybrid circuit 354 and capacitor 356 and coupled to an interior surface of the IMD housing cover (not shown) along coupling area 318. As generally shown previously in FIG. 11, extender 322 will extend between flexible circuit 300 and hybrid circuit 358 creating greater working space for performing electrical connection between components coupled to the IMD cover and components assembled in the IMD case 352. The cover (not shown) can then be hermetically sealed to case 352. Prior to sealing the cover to case 352, the cover can be removed to allow additional manufacturing steps to be performed while maintaining electrical connection between flexible circuit 300 and hybrid circuit 354. As such, flexible circuit 300 and flexible connector circuit 320 may also be referred to as a "split" flexible circuit since electrical connection between the transducer 312 included in flexible circuit 300 and the hybrid circuit 354 is accomplished via the flexible connector circuit 320.

While flexible circuits described herein have included a telemetry antenna, it is recognized that the antenna may be excluded from the flexible circuit arrangements described herein. Other IMD electrical or electronic components may be added to or substituted for the antenna and piezoelectric transducer shown incorporated in the flexible circuits described herein. The flexible circuit configurations and methods described herein allow one or more electrical component(s) to be positioned in an IMD cover and be electrically connected to circuitry positioned in the IMD case.

It is recognized that numerous electrical connection methods may be used for electrically coupling the electrical contact portion of the flexible connector circuits described herein to a hybrid circuit board. Such methods may involve direct coupling to the contacts using laser ribbon bonding, soldering, welding, or brazing. Other methods may use a variety of electrical connector elements coupled to the contacts for facilitating stable reliable connection to contact pads on the hybrid circuit. FIGS. 15A through 17B illustrate different embodiments of electrical connector elements used to electrically coupling a flexible connector circuit to a hybrid circuit board.

FIG. 15A is a plan view of a flexible circuit having an alternative electrical connector element. Flexible circuit 400 includes a piezoelectric transducer 412 incorporated in a flexible substrate 414 and electrically coupled to a flexible connector circuit 416, formed as a continuous extension of flexible substrate 414. A coupling area 418 is provided for mounting circuit 400 along an interior housing surface. Connector circuit 416 includes a laterally extending arm portion 420, an elongated serpentine extender portion 422, and a electrical contact portion 424. Electrical contact portion 424 includes electrical contacts 426 over which a compression cover 428 is installed. Compression cover 428 is a plastic molded component fitting over and exposing contacts 426.

FIG. 15B is a top plan view of a hybrid circuit 450 assembled in an IMD case 452. A surface mount base 454 is coupled to hybrid circuit 450. The surface mount base 454 includes a molded plastic open box frame 456 for receiving compression cover 428. Compression cover 428 is snapped into frame 456. Frame 456 includes a retention ledge 458 for engaging and retaining compression cover 428. Surface mount base 454 further includes contact pads 460, electrically coupled to hybrid circuit 450, which become electrically engaged with contacts 426 of flexible circuit 400 upon insertion of compression cover 428 into surface mount base 454. An elastomeric contact or zebra strip 470 may be positioned in frame 456 over contact pads 460 to facilitate quick connection between contact pads 460 and contacts 426.

Figure 16A:
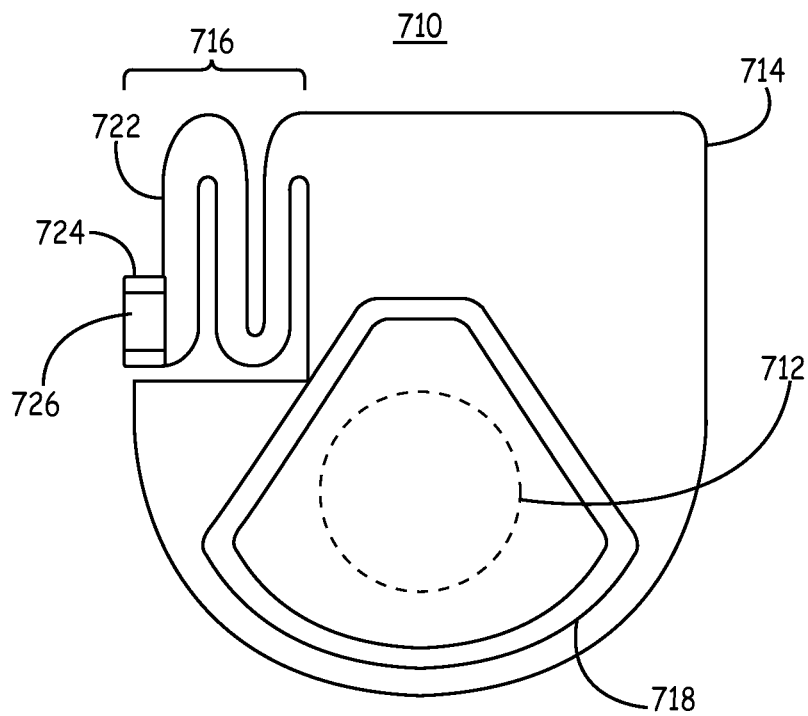
FIG. 16A is a bottom plan view of a flexible circuit having a board-to-board connector for coupling to an IMD hybrid circuit.

FIG. 16A is a bottom plan view of a flexible circuit having a board-to-board connector for coupling to an IMD hybrid circuit. Flexible circuit 710 includes a piezoelectric transducer 712 coupled to a flexible circuit substrate 714 carrying a telemetry antenna 718. A flexible connector circuit 716 includes a serpentine extender portion 722 extending from flexible substrate 714 and an electrical contact portion 724. A board-to-board connector 726, also sometimes referred to as a flex-to-board connector, is soldered to contacts (not shown) formed on electrical contact portion 724.

Figure 16B:
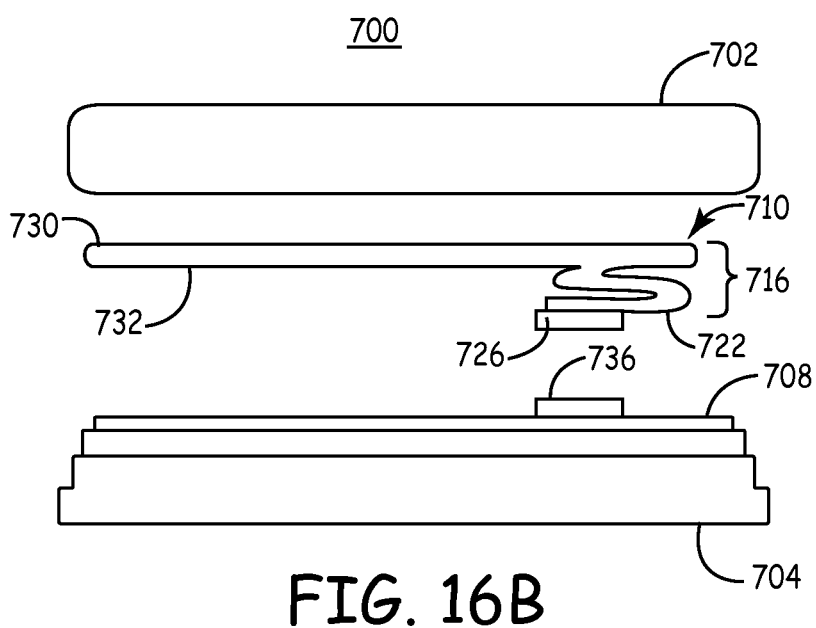
FIG. 16B is an exploded side view of the flexible circuit of FIG. 16A and an associated IMD.

FIG. 16B is an exploded side view of the flexible circuit 710 being assembled in an associated IMD 700. The top surface 730 of flexible circuit 710 is mounted to the interior surface of cover 702. Bottom surface 732 faces toward a hybrid circuit 708 assembled within case 704. A board-to-board connector 736 is soldered or otherwise surface mounted and electrically coupled to hybrid circuit board 708 for making electrical connection with board-to-board connector 726. It is recognized that the male-female arrangement of connectors 726 and 736 is interchangeable. Connectors 726 and 736 may correspond to commercially available parts, such as connectors available from Molex, Lisle, Ill.

During an assembly method, board-to-board connectors 726 and 736 are snapped together and flexible circuit 710 is mounted inside cover 702. Flexible connector circuit 716 allows extension of connector 726 away from flexible connector circuit 710 to facilitate this process.

Figure 17A:
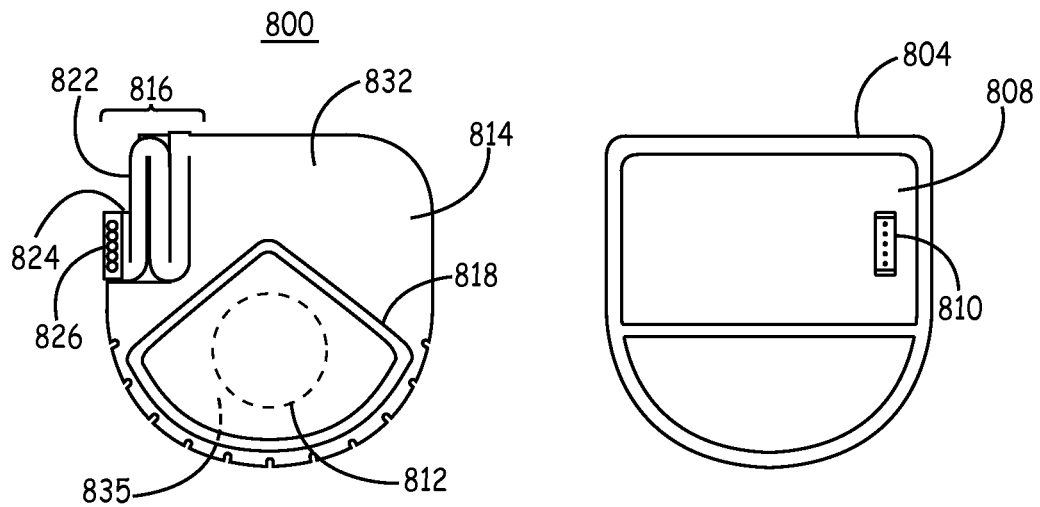
FIG. 17A is a bottom plan view of a flexible circuit including an antenna and a piezoelectric transducer incorporated in a flexible substrate.

FIG. 17A is a bottom plan view of a flexible circuit 800 including an antenna 818 and a piezoelectric transducer 812 incorporated in a flexible substrate 814. The flexible substrate 814 includes a ground plane and conductive traces (not shown) as generally described above for achieving electrical connection to antenna 818 and transducer 812. Conductive traces extend to flexible connector circuit 816 including a serpentine extender portion 822 and electrical contact portion 824. A socket connector 826 is electrically coupled to the traces along electrical contact portion 824 by soldering, welding, brazing, or other suitable coupling methods. A topside coupling area 835 is mounted against an interior surface of an IMD housing cover (not shown) to position piezoelectric transducer 812 against the housing. The bottom side 832 shown will face the hybrid circuit 808 assembled in a housing case 804. A pin array connector 810 is electrically coupled to and surface mounted on hybrid circuit 808 for electrically coupling hybrid circuit 808 to flexible circuit 800 via socket connector 826. During assembly, the socket connector 826 is pressed down over pin array connector 810 to make electrical connection, before or after mounting flexible circuit 800 to the interior of the IMD housing cover, facilitated by expansion of extender 822 from its normally flat, planar geometry.

Figure 17B:
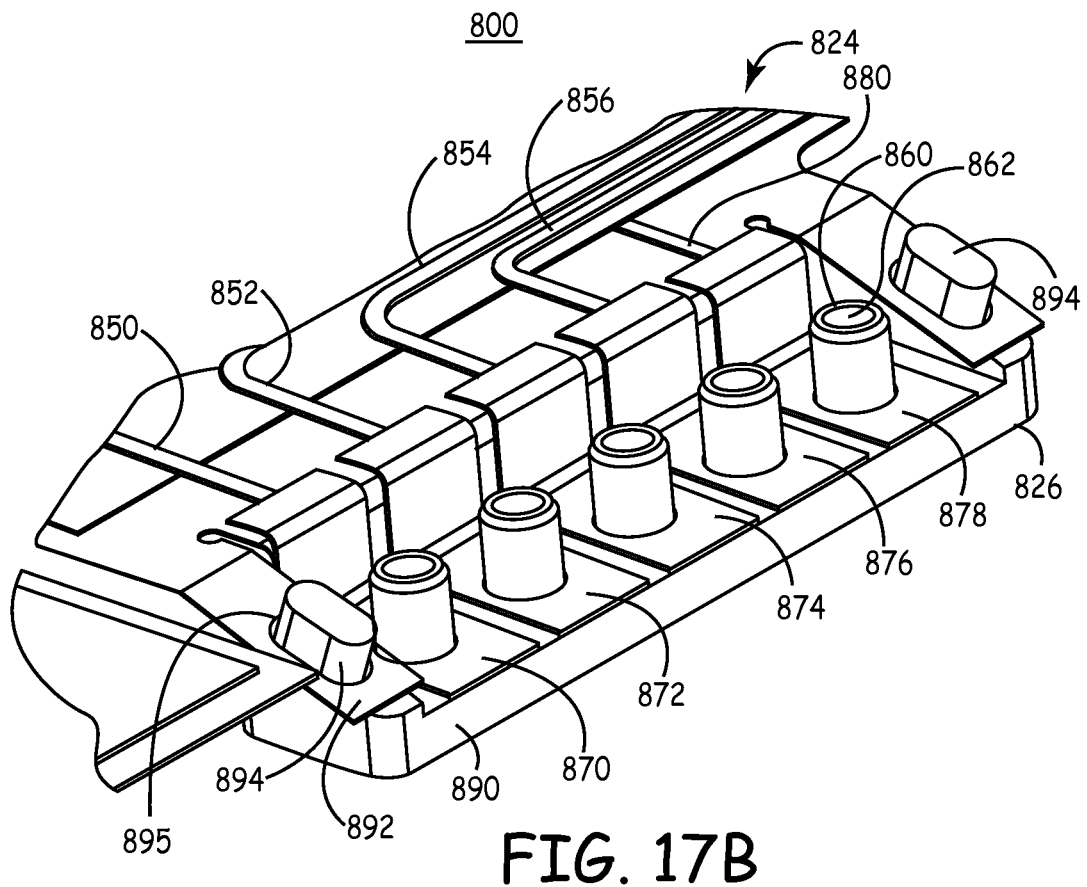
FIG. 17B is a detailed perspective view of the electrical contact portion of the flexible circuit of FIG. 17A.

FIG. 17B is a detailed perspective view of the electrical contact portion 824 and socket connector 826 with a cover layer of the flexible circuit substrate removed. Socket connector 826 includes multiple sockets 860 each coupled to respective contact pads 870 through 878. A pair of antenna traces 850 and 852 extending through flexible connector circuit 816 is electrically coupled to contact pads 870 and 872. A pair of transducer traces 854 and 856 corresponding to a brass attachment and a ceramic attachment as generally described above, are coupled to connector pads 874 and 876. A ground trace 880 extending from a ground plane within flexible substrate 814 is coupled to contact pad 878. Each socket 860 has an open receptacle 862 for receiving a pin in pin array connector 810 (FIG. 17A).

Socket connector 826 is shown coupled to electrical contact portion 824 using a heat staking process. Stakes 894 extend upward from a frame 890 on which sockets 860 and contact pads 870 through 878 are mounted. Stakes 894 and frame 890 may be formed as a single, plastic molded component. Tabs 892 are formed in the electrical contact portion 824 of flexible connector circuit 816 and positioned over stakes 894. Stakes 894 thus extend upward through openings 895 of tabs 892. During the heating process, stakes 894 are melted and deformed to retain tabs 892 thereby securely coupling socket connector 826 to flexible circuit 800.

Figure 18A:
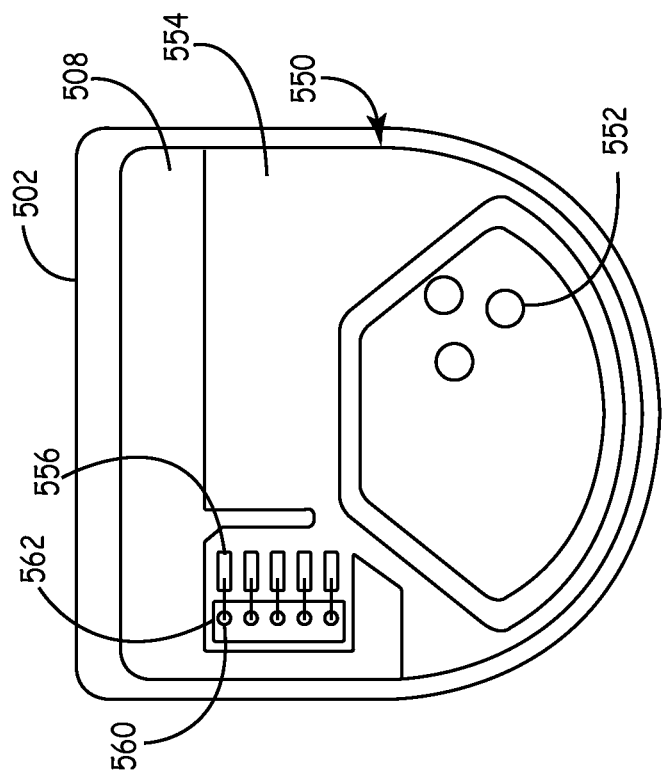
FIG. 18A is a bottom plan view of an IMD cover.
Figure 18B:
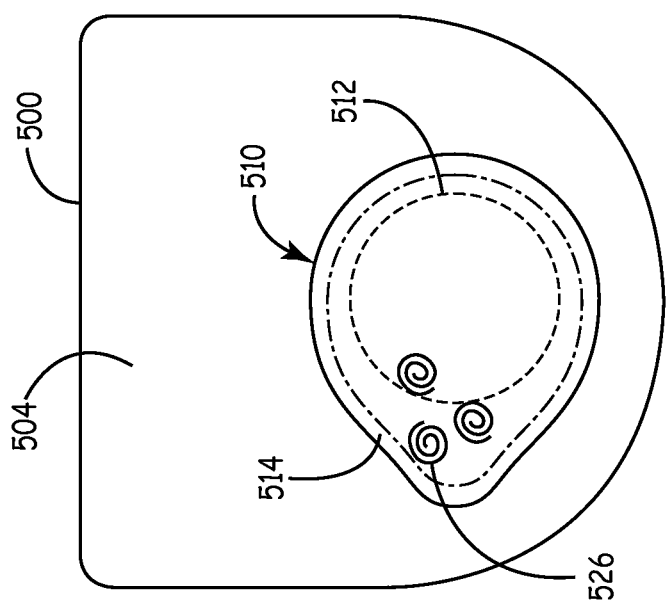
FIG. 18B is a top plan view of an IMD case including alternative electrical connection to the flexible circuit.

In alternative embodiments of the present invention, an electrical connection is made between a flexible circuit including an IMD component mounted to the interior surface of the IMD cover and the IMD hybrid circuit assembled in the IMD case using a spring connector element. FIG. 18A is a bottom plan view of an IMD cover 500, and FIG. 18B is a top plan view of an IMD case 502 in which a spring connector element is used. A flexible circuit 510 including a piezoelectric transducer 512 incorporated in a flexible substrate 514 is coupled to the interior surface 504 of cover 500 using, for example, a pressure sensitive adhesive. A flexible antenna circuit 550 is assembled in case 502, overlying hybrid circuit 508 as generally described above. Flexible circuit 510 is coupled to flexible antenna circuit 550 via spring connector elements 526. Spring connector elements 526 are shown as helical springs which compress into themselves for a relatively flat geometry upon compression against contact pads 552 when cover 500 is joined to case 502. As such, spring connector elements 526 assume a relatively flattened geometry upon closure of the ICD case and cover. The flattened geometry corresponds to a predictable compressed shape of the spring connector element thus providing consistent routing of the electrical connection elements upon closure of the case and cover. No bending, curving or kinking of the spring connector elements 526 is required. Unintended compression of other ICD components and unintended strain introduced upon connector elements 526 is avoided. The ICD cover may be removed from the case prior to welding to allow testing or other procedures to be performed, however, electrical connection between the flexible circuit 510 still mounted to the ICD cover and the hybrid circuit 508 will be lost.

Spring connector element 526 may alternatively be embodied as coiled springs having a constant coil diameter or an expanding coil diameter or as leaf springs or stamped springs. In each of these embodiments, the spring connector element will assume a relatively more flattened geometry upon closure of the case and cover and provide consistent routing of the electrical connection between the flexible circuit 510 and hybrid circuit 508. Contact pads 552 may be formed oversized to ensure alignment and electrical connection with spring connector elements 526.

Spring connector elements 526 are coupled to traces extending through flexible substrate 514 to a jumper (not shown) or other electrical contacts which provide electrical connection to a brass attachment point and a ceramic attachment point of transducer 512 as generally described in conjunction with FIG. 3. A third spring connector element 526 is coupled to a ground plane (not shown) embedded in flexible substrate 514.

Contact pads 552 are likewise coupled to traces (not shown) extending within flexible substrate 554 to contacts 556, which are electrically coupled to corresponding contact pads 560 on hybrid circuit 508, for example using laser ribbon bonds 562. As such, spring connector elements 526 provide electrical coupling across the cover 500 and case 502 while enabling a top down assembly method for stacking components in the case then closing the case 502 with cover 500 and completing electrical connection of the flexible circuit 510 to hybrid circuit 508 via antenna flexible circuit 550. Re-opening of the case 502 and cover 500 for additional manufacturing or testing processes remains possible prior to laser welding the cover to the case with flexible circuit 510 remaining mounted to cover 504.

Figure 19B:
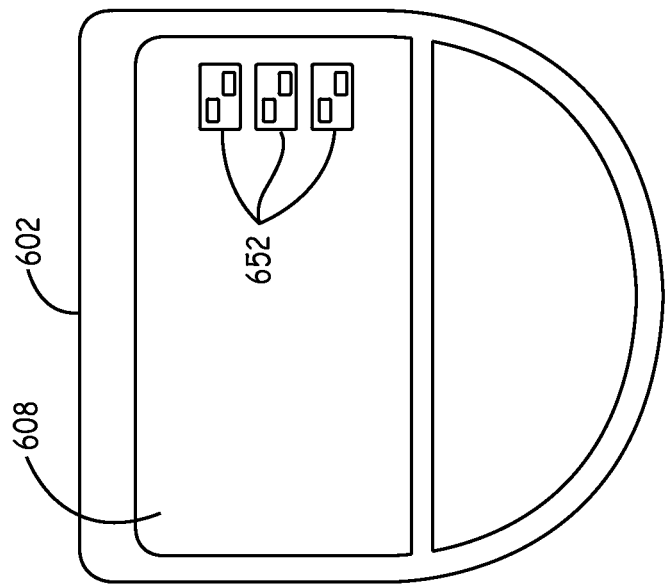
FIG. 19B is a top plan view of an IMD case according to an alternative embodiment of the invention.
Figure 19A:
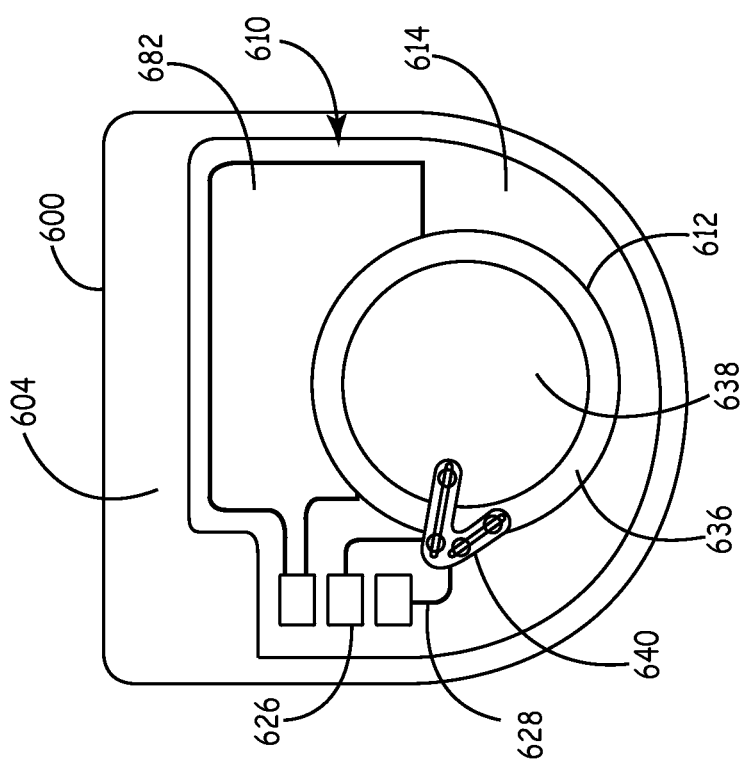
FIG. 19A is a bottom plan view of an IMD cover.

FIG. 19A is a bottom plan view of an IMD cover 600, and FIG. 19B is a top plan view of an IMD case 602 according to an alternative embodiment of the invention. In this embodiment, electrical contacts 626 are formed on flexible circuit 610 and spring connector elements 652 are mounted on hybrid circuit 608. Flexible circuit 610 is mounted to the interior surface 604 of cover 600. One of the contacts 626 is coupled to an embedded ground plane 682 within flexible circuit substrate 614, and the other contacts 626 are coupled to conductive traces 628 formed in flexible substrate 614. Traces 628 extend to the brass and ceramic portions 636 and 638, respectively, of transducer 612 via jumper 640.

Oversized contacts 626 become electrically coupled to spring connector elements 652 upon closure of cover 600 and case 602. Spring connector elements 652 are mounted on and electrically coupled to hybrid circuit 608. Spring connector elements 652 may be welded, bonded, soldered or brazed to mechanically and electrically join elements 652 to hybrid circuit 608. Hybrid circuit 608 is assembled within case 602. Spring connector elements 652 may be implemented as a coiled spring, leaf spring, stamped spring, or a clip-type spring as shown in FIG. 19B, which may correspond to a commercially available compression connector such as Model Number MIH-2-412-TF connector available from J.S.T. Mfg. Co., Ltd., Waukegan, Ill. USA. Spring connector elements 652 assume a predictable compressed geometry that is relatively flattened upon closure of the case 602 and cover 600, providing a flattened geometry with consistent routing of the electrical connection between the flexible circuit 610 and hybrid circuit 608 when the case 602 and cover 600 are closed.

Thus, an IMD and methods for assembly have been presented in the foregoing description with reference to specific embodiments. It is appreciated that various modifications to the referenced embodiments may be made without departing from the scope of the invention as set forth in the following claims.

The invention claimed is:
1. An implantable medical device, comprising:
a hermetic housing comprising a case and a cover, the case and the cover each having an interior surface;
a piezoelectric transducer incorporated into a first flexible circuit mounted to the interior surface of the cover, the piezoelectric transducer having a first electrical contact;
a hybrid circuit assembled in the case;
means for electrically coupling the piezoelectric transducer to the hybrid circuit assembled in the case, the electrical coupling means comprising an elongated flexible circuit having a normally planar geometry and comprising an extender portion extending between a proximal end attached to the first flexible circuit and a free distal end, a second electrical contact positioned along the extender free distal end and electrically coupled to the hybrid circuit, and a conductive trace extending along the extender portion from the second electrical contact and electrically coupled to the first electrical contact, the elongated flexible circuit expanding from its normally planar geometry to flexibly extend the second electrical contact away from the first flexible circuit when the cover is removed from the case while maintaining electrical coupling between the first electrical contact and the hybrid circuit, the elongated flexible circuit resuming the planar geometry upon closure of the case and the cover; and
a second flexible circuit comprising an antenna, the second flexible circuit overlaying the hybrid circuit assembled in the case and having a third electrical contact formed on a top surface of the second flexible circuit, a conductive trace extending from the third electrical contact and electrically coupled to the hybrid circuit, the second electrical contact being electrically coupled directly to the third electrical contact, the piezoelectric transducer nesting within the antenna upon closure of the case and the cover.

2. The device of claim 1 wherein the elongated the extender portion of the elongated flexible circuit having an elongated serpentine configuration.

3. The device of claim 2 wherein the electrical coupling means comprises a compression cover over the second electrical contact and a surface mounted frame positioned on the hybrid circuit for receiving the compression cover.

4. The device of claim 3 wherein the surface mounted frame comprises an elastomeric connector for coupling the second electrical contact to the hybrid circuit.

5. The device of claim 2 wherein the electrical coupling means elongated flexible circuit comprises a socket connector coupled to the elongated flexible circuit and a pin array connector surface mounted on the hybrid circuit for electrically coupling to the socket connector.

6. The device of claim 2 wherein the electrical coupling means comprises a first board-to-board connector coupled to the elongated flexible circuit and a second board-to-board connector surface mounted on the hybrid circuit for receiving the first board-to-board connector.

7. The device of claim 1 wherein the elongated flexible circuit being a unitary circuit.

8. An implantable medical device (IMD), comprising:
a hermetic housing comprising a case and a cover, the case and the cover each having an interior surface, the interior surfaces of the case and the cover defining an interior space of the housing;
a hybrid circuit assembled in the case;
a first flexible circuit coupled to the interior surface of the cover, the flexible circuit having a top surface positioned against the interior surface of the cover and a bottom surface facing toward the interior space of the housing, the flexible circuit comprising
a flexible substrate comprising a first layer of flexible insulating material forming the top surface, a second layer of flexible insulation material forming the bottom surface, and a copper layer positioned between the first and second layers,
an IMD component positioned along the second layer,
a cover layer positioned over the IMD component;
an elongated flexible circuit extending from the flexible substrate and having a free distal end, the elongated flexible circuit comprising a first electrical contact at the free distal end and a conductive trace formed in the copper layer extending from the IMD component to the first electrical contact,
the first electrical contact electrically coupled to the hybrid circuit,
the elongated flexible circuit having a normally planar geometry and expanding from the normally planar geometry to flexibly extend the first electrical contact away from the first flexible circuit mounted to the interior surface of the cover toward the hybrid circuit assembled in the case when the cover and case are open and regaining the normally planar geometry when the case and cover are closed.

9. The device of claim 8 wherein the IMD component being a piezoelectric transducer.

* * * * *